United States Patent
Yamamoto et al.

(10) Patent No.: US 6,925,612 B2
(45) Date of Patent: Aug. 2, 2005

(54) DEVICE AND METHOD FOR SELECTING ELECTROPHORESIS BAND

(75) Inventors: Noriyuki Yamamoto, Kanagawa (JP); Takuro Tamura, Kanagawa (JP); Toshimasa Watanabe, Kanagawa (JP)

(73) Assignee: Hitachi Software Engineering Co., LTD, Kanagawa (JP)

(*) Notice: Subject to any disclaimer, the term of this patent is extended or adjusted under 35 U.S.C. 154(b) by 570 days.

(21) Appl. No.: 09/895,338

(22) Filed: Jun. 29, 2001

(65) Prior Publication Data

US 2002/0039435 A1 Apr. 4, 2002

(30) Foreign Application Priority Data

Sep. 14, 2000 (JP) ........................... 2000-279861

(51) Int. Cl.⁷ ............................................. G09G 5/00
(52) U.S. Cl. .................. 715/860; 715/809; 382/129; 382/133; 382/139; 204/450; 204/452; 204/603
(58) Field of Search ........................... 715/772, 809, 715/970, 859, 860, 861; 382/128, 129, 131, 132, 133, 139, 134, 140; 204/461, 451, 452, 450, 456, 603, 612; 345/856, 857, 858, 859, 860, 861, 862, 863, 788, 764

(56) References Cited

U.S. PATENT DOCUMENTS

| | | | | |
|---|---|---|---|---|
| 4,592,089 A | | 5/1986 | Hartman | |
| 5,904,822 A | * | 5/1999 | Casavant | 204/461 |
| 6,101,265 A | * | 8/2000 | Bacus et al. | 382/133 |
| 6,597,383 B1 | * | 7/2003 | Saito | 345/850 |
| 2002/0081092 A1 | * | 6/2002 | Ozawa et al. | 386/46 |

* cited by examiner

Primary Examiner—Ba Huynh
(74) Attorney, Agent, or Firm—Reed Smith LLP; Stanley P. Fisher, Esq.; Juan Carlos A. Marquez, Esq.

(57) ABSTRACT

The present invention aims at easy and efficient selection of bands present on a lane.

A region 502 is set on a display of a lane 503 having a plurality of bands 504 to 508, based on an input cursor 501 of a pointing unit. The bands 506 to 508 within the region 502 are displayed to be in a selection candidate state. The size of the region 502 may be altered by an input of a predetermined key of a keyboard. Along with the size alteration of the region 502, bands to be displayed in the selection candidate state also change. By selecting with the mouse button, a band of interest is accurately selected from the bands in the selection candidate state.

8 Claims, 14 Drawing Sheets

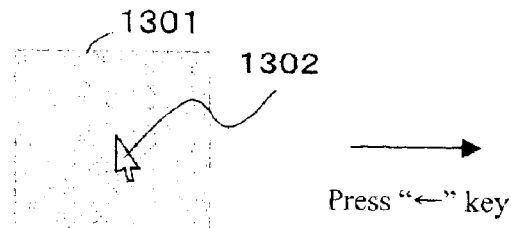
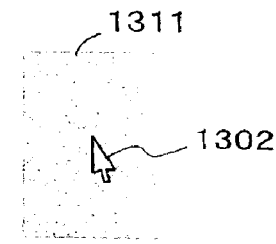
Fig. 13A     Fig. 13B
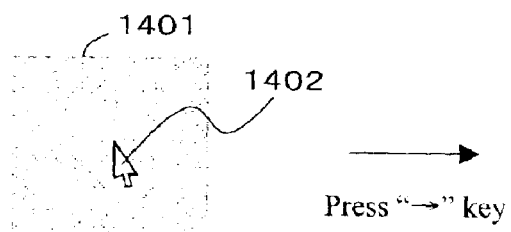
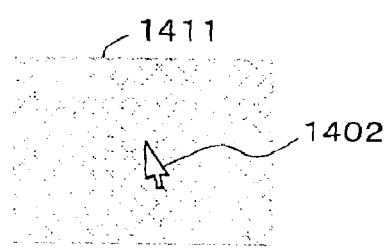
Fig. 14A     Fig. 14B
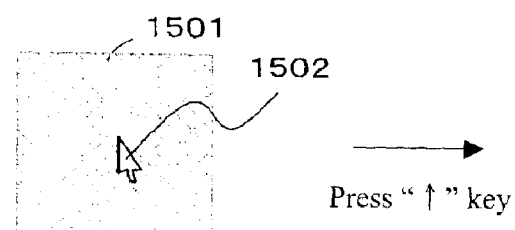
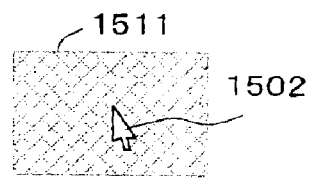
Fig. 15A     Fig. 15B
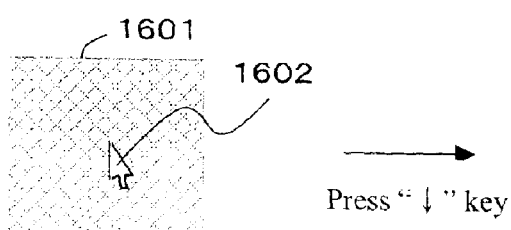
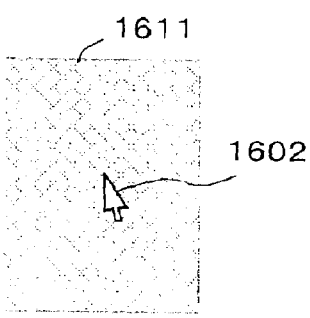
Fig. 16A     Fig. 16B

Fig. 18

Structure of data memory

| Number of lanes | N | |
|---|---|---|
| Lane 1 data | Center coordinates (Y1U, X1S) of the upper end of Lane 1 | |
| | Width (W1S) of upper end of Lane 1 | |
| | Center coordinates (Y1E, X1E) of the lower end of Lane 1 | |
| | Width (W1E) of the lower end of Lane 1 | |
| | Number of bands (M1) in Lane 1 | |
| | Band data of Lane 1 | Relative coordinates (D1-1) of Band 1 with respect to the upper end of Lane 1 |
| | | Relative coordinates (D1-2) of Band 2 with respect to the upper end of Lane 1 |
| | | : |
| | | Relative coordinates (D1-M1) of Band M1 with respect to the upper end of Lane 1 |
| Lane 2 data | | |
| : | | |
| Lane N data | | |

DEVICE AND METHOD FOR SELECTING ELECTROPHORESIS BAND

PRIORITY INFORMATION

This application claims priority to Japanese Application Serial No. 279861/2000, filed Sep. 14, 2000.

FIELD OF THE INVENTION

The present invention relates to a device and a method for selecting an electrophoresis band. More particularly, the present invention relates to a user interface for simply and accurately selecting a band of interest from bands established on an image data, on a display screen displaying the image data obtained by picking up an electrophoresis pattern of a sample.

BACKGROUND OF THE INVENTION

In biochemical experiments, samples containing molecules such as DNA with various lengths are sometimes separated by electrophoresis. By electrophoresis, molecules such as DNA or proteins migrate on a gel by the application of an electric field, thereby being separated and established as bands according to their molecular weights. A range where bands have migrated from the same initial migration point is defined as a lane.

FIG. 19 is a schematic diagram of an electrophoresis device. Hereinafter, separation of DNA molecules will be described as an example. The electrophoresis device 1903 is provided with a negative (−) electrode 1904 and a positive (+) electrode 1905, which are connected to a power source 1901 via a conductor 1902. A sample is put into a sample inlet 1906 on the (−) electrode 1904 side, and a voltage is applied. As a result, negatively-charged DNA molecules are electrically pulled and thus migrate from the (−) electrode 1904 side toward the (+) electrode 1905 side. According to the difference of the molecular weights, the molecules are separated into a DNA molecule 1908 of a larger molecular weight, a DNA molecule 1909 of a middle molecular weight and a DNA molecule 1910 of a small molecular weight. The path where these DNA molecules have migrated is a lane 1915. The states of the DNA molecules separated on the lane 1915 can be observed with a CCD camera or the like, and may be analyzed by image processing.

For image processing, the DNA molecules present on the lane 1915 are established as bands on an image of the post-migration DNA molecules. The bands can be established automatically by reading the brightness of pixels on the lane, integrating the brightness in the migration direction 1907 from the sample inlet 1906 and in the direction perpendicular to the migration direction 1907, and detecting a peak position 1917 from a generated spectrum 1916. Then, lines perpendicular to the migration direction 1907 are drawn on the lane 1915 at positions corresponding to the peak positions, thereby setting a band 1911 (the DNA molecule 1908), a band 1913 (the DNA molecule 1909) and a band 1914 (the DNA molecule 1910).

When the lane 1915 is contaminated by dust 1919, the dust 1919 will appear as a peak 1918 on the spectrum 1916, and could be mistakenly detected as a band 1912. In order to carry out the experiment, the setting of the error band 1912 must be cleared. For this purpose, the image processor is provided with a band selecting function. In general, in order to select a band, an operator inputs a band selecting command with a pointing unit such as a mouse looking at the bands displayed on the image display unit. When the band to be selected is too small or too narrow to be selected with the pointing unit, a predetermined range of the band displaying region is enlarged to ease the selection.

In order to select a band on the image with the pointing unit such as a mouse according to the band selecting function of a conventional image processor, the cursor of the pointing unit must accurately point the band of interest on the lane displayed on the image display unit. Furthermore, when the band of interest is very close to another band or is in the middle of a group of gathering bands, the band regions overlapping in the image makes it difficult or impossible to designate the band of interest with the pointing unit.

In view of such problems of an image processor for processing electrophoresis image data, the present invention has an objective of providing a device and method for simply and efficiently selecting and displaying a band present on a lane.

SUMMARY OF THE INVENTION

In order to accomplish the above-described objective, the device of the present invention is provided with an image memory for storing electrophoresis image data, an image display input unit for performing input on a display screen displaying the image data, and a processor for selecting bands of the image data by inputting a selection region on a lane with a pointing unit and inputting a selection command to the image data on the display screen with a keyboard. Based on the input of the selection region of the lane and the selection command, the bands to be selected are determined and displayed in a selection candidate state distinctively from other bands on the screen of the image display input unit.

Instead of inputting the selection region and the selection instruction with the pointing unit alone, the pointing unit may be used together with a keyboard to select a band of interest in an easier and more accurate manner.

According to the present invention, a device for selecting an electrophoresis band of interest from a plurality of bands on an electrophoresis lane of a sample comprises: a display unit for displaying an image of the plurality of bands established on the lane; a region setting unit for setting a region on the lane on a screen of the display unit; a region altering unit for altering the size of the region; a selection candidate displaying unit for displaying bands within the region in a selection candidate state; and a band selecting unit for processing the bands in the selection candidate state to be in a selection state.

Display in the selection candidate state refers to a clear distinction of the selection candidates such as a display with a different color or a blinking display which is different from a usual display. The bands in the selection candidate state may be processed to be in a selection state (the bands may be selected for sure) with a band selecting unit, for example, by clicking a mouse button or by pressing an enter key of a keyboard.

Preferably, the region setting unit sets the region on the lane by setting an input cursor of a pointing unit on the lane at the center, and the region altering unit alters the size of the region in accordance with the press of a predetermined key of a keyboard.

Preferably, the device further comprises a band information displaying unit for displaying the number of bands in the selection candidate state relative to the region.

According to the present invention, a device for selecting an electrophoresis band of interest from a plurality of bands on an electrophoresis lane of a sample, comprises: a display unit for displaying an image of the plurality of bands established on the lane; a region setting unit for setting a region on the lane on a screen of the display unit; a selection candidate displaying unit for displaying one of the bands within the region, in a selection candidate state; a selection candidate display altering unit for altering the band in the selection candidate state to a band immediately before or after the former band along the lane; and a band selecting unit for processing the band in the selection candidate state to be in a selection state.

Preferably, the region setting unit sets the region on the lane based on a position of an input cursor of a pointing unit on the lane (e.g., where the position of the input cursor is set the center), the selection candidate displaying unit displays a band closest to the input cursor in the selection candidate state, and the selection candidate display altering unit alters the band to be displayed in the selection candidate state in accordance with the press of a predetermined key of a keyboard.

Preferably, the device further comprises a region altering unit for altering the size of the region in accordance with the press of a predetermined key of the keyboard.

The device of the invention may further comprise a band information displaying unit for displaying information of the bands displayed in the selection candidate state relative to the region.

The information of the bands in the selection candidate state may be, for example, relative positions of the bands within the established region.

According to the present invention, a method for selecting an electrophoresis band of interest from a plurality of bands on an electrophoresis lane of a sample, comprises the steps of: setting a region on the lane based on an input cursor of a pointing unit placed on the display of the lane having a plurality of bands; displaying bands within the region in a selection candidate state; altering the size of the region in accordance with an key input of a predetermined key of a keyboard, as well as altering states of bands that became included in the region as the result of the size alteration from a normal state to the selection candidate state and states of bands that fell out from the region as the result of the size alteration from the selection candidate state to the normal state; and displaying selected bands of the bands in the selection candidate state in a selection state in response to a selection input.

The selection command may be inputted by clicking a button of a mouse (the pointing unit) or by pressing an enter key of the keyboard. By this input of the selection command, bands in the selection candidate state is processed to be in a selection state (i.e., selected for sure).

According to the present invention, a method for selecting an electrophoresis band of interest from a plurality of bands on an electrophoresis lane of a sample, comprises the steps of: setting a region on the lane based on an input cursor of a pointing unit placed on the display of the lane having a plurality of bands; displaying a band within the region, which is closest to the input cursor, in a selection candidate state; altering the band in the selection candidate state to a band immediately before or after the former band along the lane in accordance with the press of a predetermined key of a keyboard; and processing the band in the selection candidate state to be in a selection state.

BRIEF DESCRIPTION OF THE DRAWINGS

FIGS. 13A and 13B are schematic views showing an operation for reducing a size of a selection candidate region in a horizontal direction.

FIGS. 14A and 14B are schematic views showing an operation for enlarging a selection candidate region in a horizontal direction.

FIGS. 15A and 15B are schematic views showing an operation for reducing a size of a selection candidate region in a vertical direction.

FIGS. 16A and 16B are schematic views showing an operation for enlarging a selection candidate region in a vertical direction.

FIG. 18 is a diagram showing an exemplary structure of a data memory.

DETAILED DESCRIPTION OF THE INVENTION

Hereinafter, embodiments of the present invention will be described with reference to the attached drawings.

Figure 1:
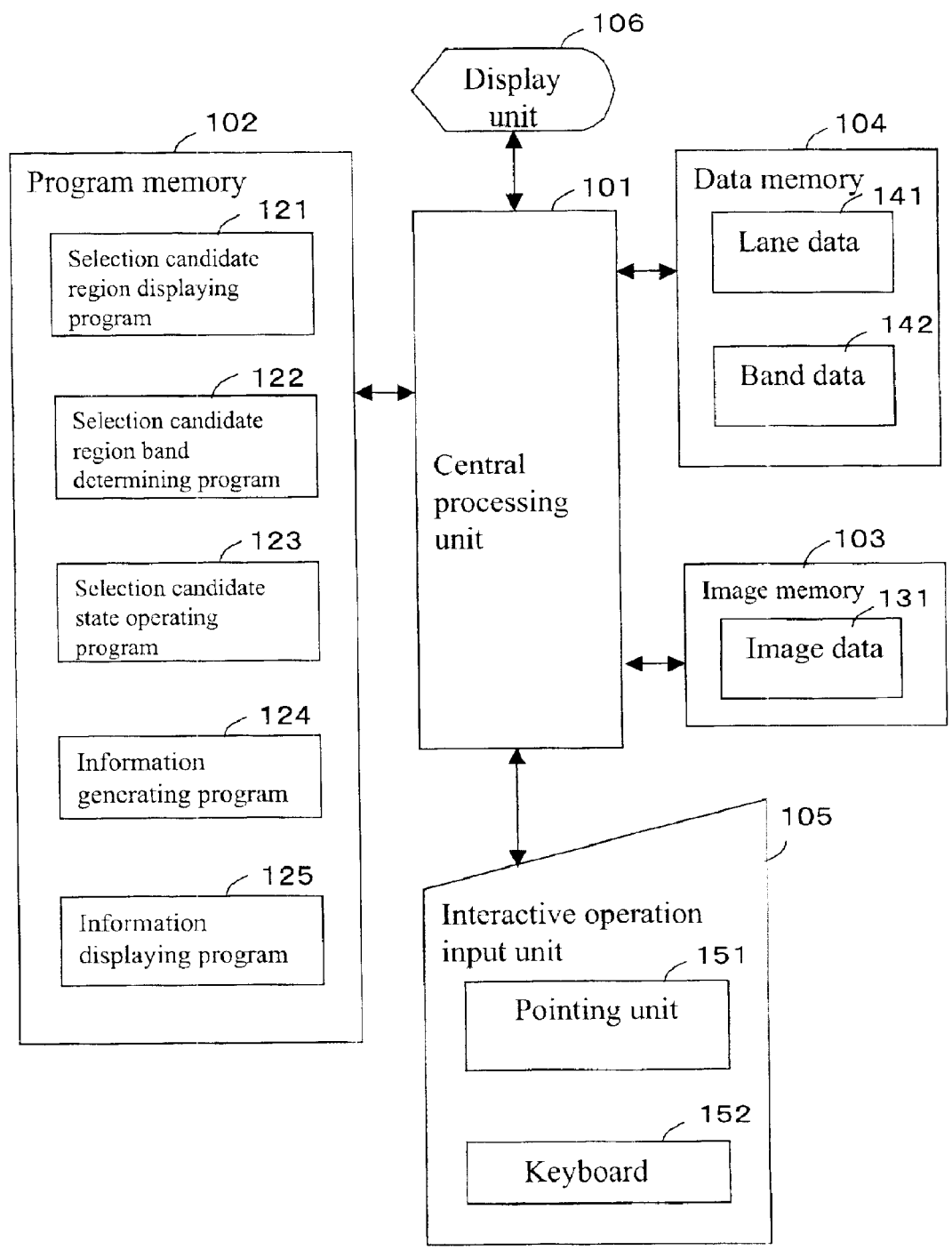
FIG. 1 is a block diagram showing an exemplary structure of a band selecting device of the invention.

FIG. 1 is a block diagram showing an exemplary structure of a device of the invention for selecting an electrophoresis band. The band selecting device is provided with a central processing unit 101 for processing various operations, a program memory 102 for storing programs necessary for the operations by the central processing unit 101, an image memory 103, a data memory 104, an interactive operation input unit 105 and a display unit 106 as a display screen.

The program memory 102 stores a selection candidate region displaying program 121, a selection candidate region band determining program 122, a selection candidate state operating program 123, an information generating program 124 and an information displaying program 125. The image memory 103 stores image data 131 obtained by picking up an image of the sample of interest. The data memory 104 stores lane data 141 which is information of the image data in an area determined as a lane, and band data 142 which is information of the image data of areas determined as bands. The lane data 141 and the band data 142 store information of the lane locations and the band locations in a coordinates data style.

A band selection operation is carried out by a computer program. The present system can be implemented in a usual manner with a personal computer or a workstation. The program recorded on a storage medium such as a magnetic storage or a CD-ROM is installed in a hard disk and executed by the central processing unit 101. Alternatively, the program may be downloaded from a network (e.g., online circuit or the Internet) into the hard disk.

FIG. 18 shows an exemplary structure of the data memory. The data memory 104 stores number of lanes N as well as the lane data. The lane data 141 stores positional data of a lane and data of bands on the lanes. The relative positions of the lane on an image are stored in the lane data 141. The positions of the bands relative to the lane are stored in band data 142 included in the data memory 104. Thus, the data memory 104 and the image memory 103 are stored in separate spaces. The lane and the bands are displayed based on the lane data 141 and the band data 143 in the data memory 104.

The selection candidate region displaying program 121 stored in the program memory 102 displays a selection candidate region on the display unit 106, where the center position is determined by an input with the pointing unit 151 (e.g., a mouse) of the interactive operation input unit 105. The selection candidate region band determining program 122 reads out the lane data 141 and the band data 142 via the operation of the central processing unit 101 to determine the presence of bands within the selection candidate region. The selection candidate state operating program 123 processes the bands that are determined by the selection candidate region band determining program 122 to be in a selection candidate state. The information generating program 124 generates information of bands within the selection candidate region. The information displaying program 125 displays the information of the bands within the selection candidate region generated by the information generating program 124 on the display unit 106.

Figure 2:
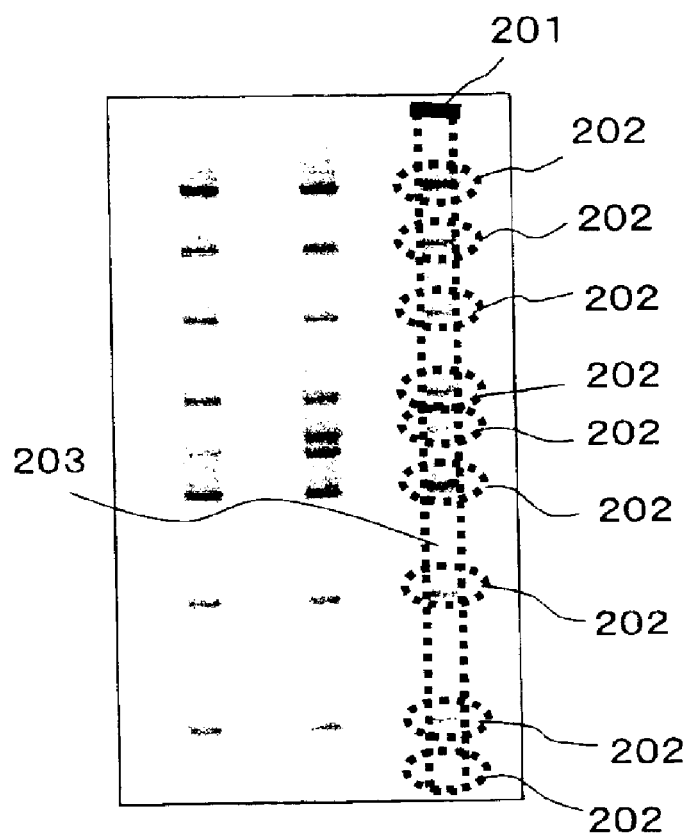
FIG. 2 is a view showing examples of lanes and bands on an electrophoresis gel.

FIG. 2 is a view of lanes and bands on an electrophoresis gel. Molecules that have migrated from the starting point 201 as a result of electrophoresis are established as bands 202. The range where the bands 202 have migrated from the single starting point 202 is set as a lane 203.

Figure 3:
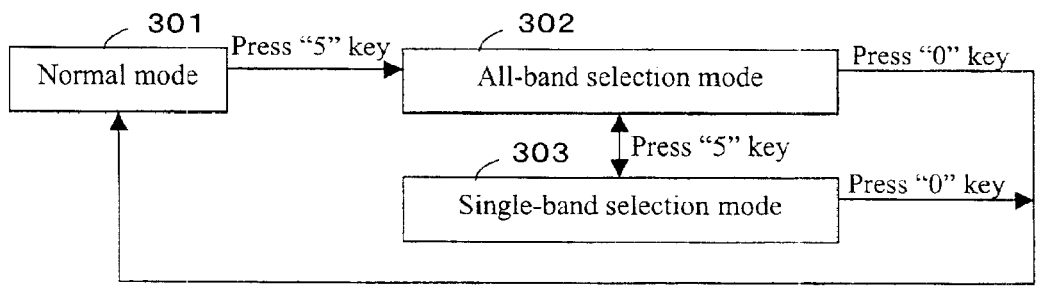
FIG. 3 is a diagram showing switching of band selection modes in accordance with a keyboard input.

FIG. 3 is a diagram showing transition of band selection modes which are switched from one to another in accordance with an input with the keyboard 152 of the interactive operation input unit 105. The band selecting device of the invention has two band selection modes, all-band selection mode for selecting all of the bands within the selected region of the lane and single-band selection mode for selecting a single band. A normal mode 301 where the selection and display of the bands are not carried out is switched to the all-band selection mode 302 by pressing a predetermined key (e.g., "5" key) on the keyboard. The all-band selection mode 302 is switched to the single-band selection mode 303 by pressing a predetermined key (e.g., "5" key) on the keyboard. The single-band selection mode 303 is switched to the all-band selection mode 302 by pressing a predetermined key (e.g., "5" key) on the keyboard. The all-band selection mode 302 and the single-band selection mode 303 can be returned to the normal mode 301 by pressing a predetermined key (e.g., "0" key) on the keyboard.

Figure 4:
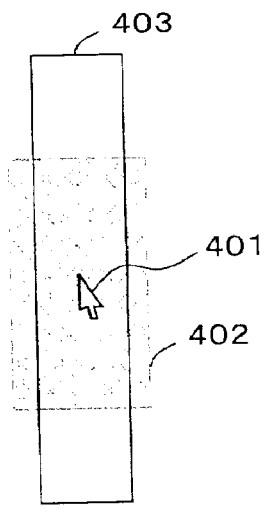
FIG. 4 is a schematic view for illustrating a display of a selection candidate region.

FIG. 4 is a schematic view for illustrating a display of the selection candidate region 402 where the input cursor 401 of the pointing unit is set at the center. When the input cursor 401 of the pointing unit of the interactive operation input unit 105 is placed on the lane 403, a selection candidate region 402 of a predetermined size is displayed for the lane 403 with the coordinates of the input cursor 401 being at the center. The size of the selection candidate region 402 may be altered as described below by using predetermined keys of the keyboard (e.g., arrow keys ",", "and").

Figure 5:
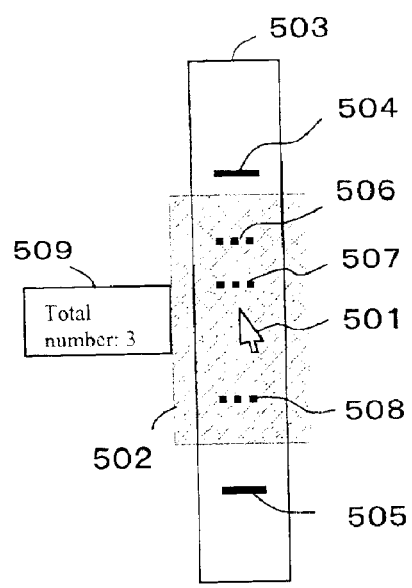
FIG. 5 is a schematic view for illustrating a selection candidate display and a band information display of bands within the selection candidate region under the all-band selection mode.

FIG. 5 is a schematic view for illustrating a selection candidate display and a band information display of the bands within the selection candidate region under the all-band selection mode. When coordinates are designated with an input cursor 501 of the pointing unit, a selection candidate region 502 is displayed on a lane 503 with the designated coordinates being at the center as described above. Bands 504 and 505 outside the selection candidate region 502 are represented by solid lines as usual display, whereas bands 506, 507 and 508 within the selection candidate region 502 are represented by broken lines as a selection candidate display. Instead of representing the bands within the selection candidate region 502 by broken lines as in the figure, they may alternatively be displayed by any other style (e.g., different color or blinking display) as long as they are distinct from other bands. When the input cursor 501 moves on the lane 503, the position of the selection candidate region 502 also moves on the lane 503, according to which the selection candidate bands also change.

Information such as the number of bands within the selection candidate region 502 is displayed as selection candidate region band information 509 in the vicinity of the selection candidate region 502. In the case of FIG. 5, the selection candidate region band information 509 tells that three bands are present in the selection candidate region 502. The size of the selection candidate region 502 may be altered as described below by a keyboard operation. As the size of the selection candidate region 502 is altered, the selection candidate bands and selection candidate region band information 509 also change.

Figure 6:
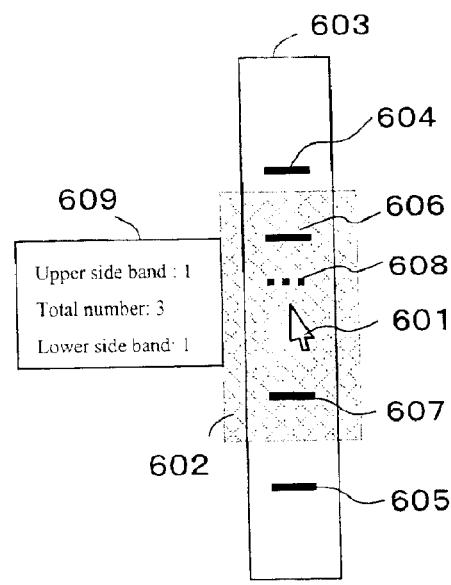
FIG. 6 is a schematic view for illustrating a selection candidate display and a band information display of bands within the selection candidate region under the single-band selection mode.

FIG. 6 is a schematic view for illustrating a selection candidate display and a band information display of the bands within the selection candidate region under the single-band selection mode. When coordinates are designated with an input cursor 601 of the pointing unit, a selection candidate region 602 is displayed on a lane 603 with the coordinates designated by the cursor 601 being at the center as described above. Bands 604 and 605 outside the selection candidate region 602 are represented by solid lines as usual display, whereas a band 608 which is the closest band to the input cursor 601 of the pointing unit within the selection candidate region 602 is represented by a broken line as a selection candidate display. Other bands 606 and 607 are represented by solid lines as a usual display although they are present within the selection candidate region. When the input cursor 601 moves on the lane 603, the position of the selection candidate region 602 also moves on the lane 603, according to which the selection candidate band also changes to a band closest to the input cursor.

Information such as the number of bands within the selection candidate region 602 is displayed as selection candidate region band information 609 in the vicinity of the selection candidate region 602. In the case of FIG. 6, the selection candidate region band information 609 tells that total of three bands are present in the selection candidate region 602 and that one band is present above and one band is present under the selection candidate display band. The size of the selection candidate region 602 may be altered as described below by a keyboard operation. As the size of the selection candidate region 602 is altered, the selection candidate region band information 609 also changes.

Figure 7:
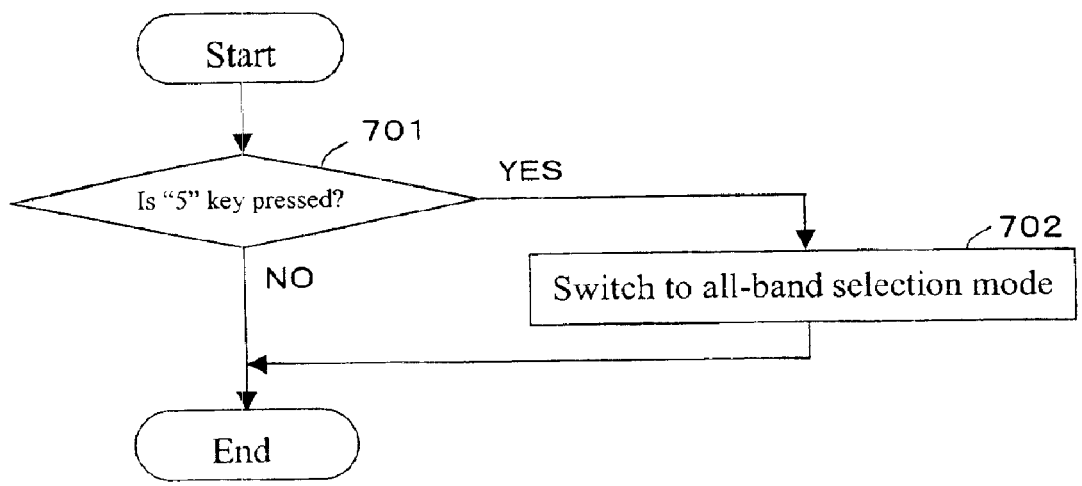
FIG. 7 is a flowchart showing a process under a normal mode.

FIG. 7 is a flowchart showing a process under the normal mode. In step 701, whether or not the "5" key of the keyboard is pressed is checked. If the "5" key is determined to be pressed, the process proceeds to Step 702 to switch to the all-band selection mode and ends. If the "5" key is determined to be unpressed, the process ends without any operation.

Figure 8:
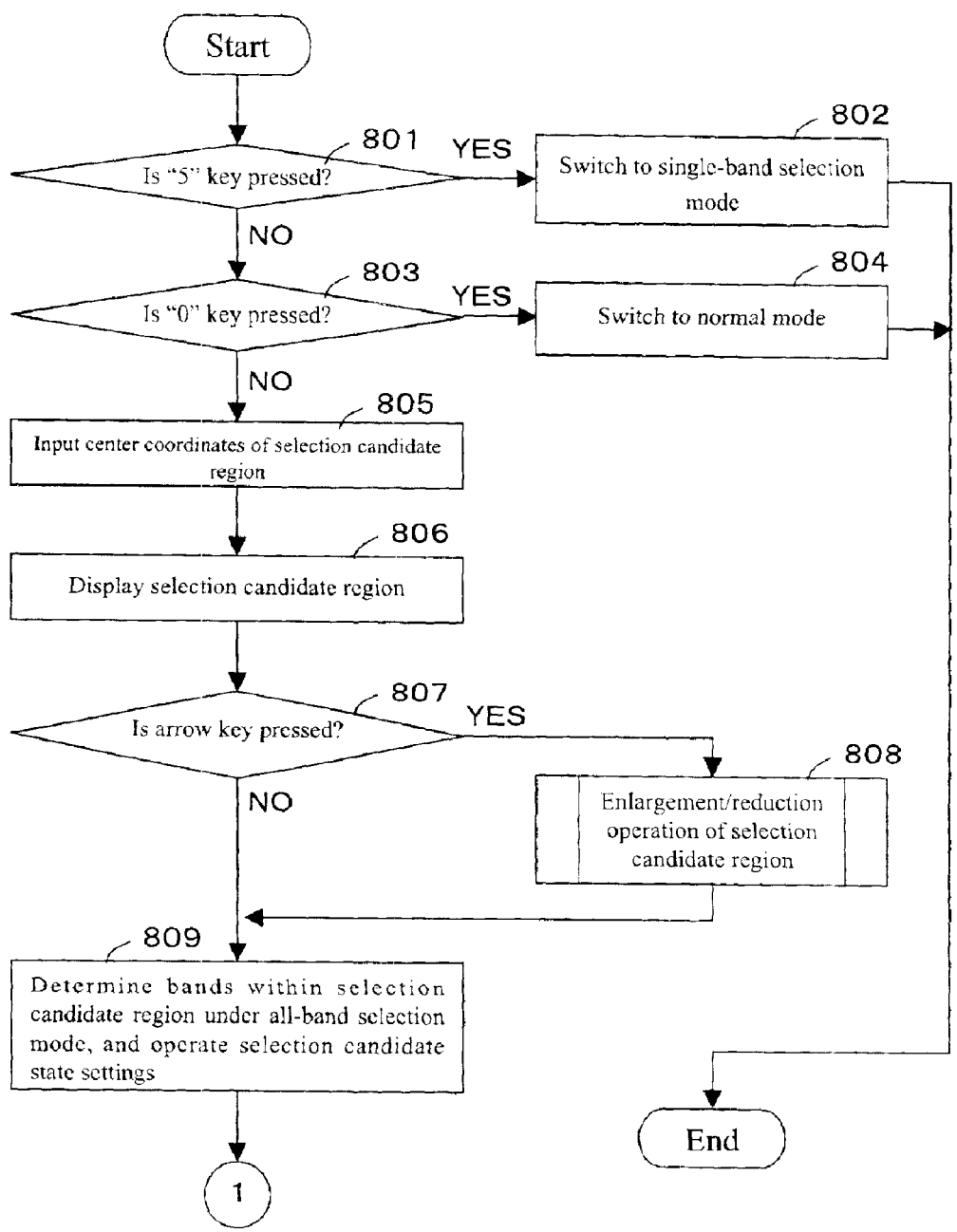
FIG. 8 is a flowchart for showing a general process under the all-band selection mode.
Figure 9:
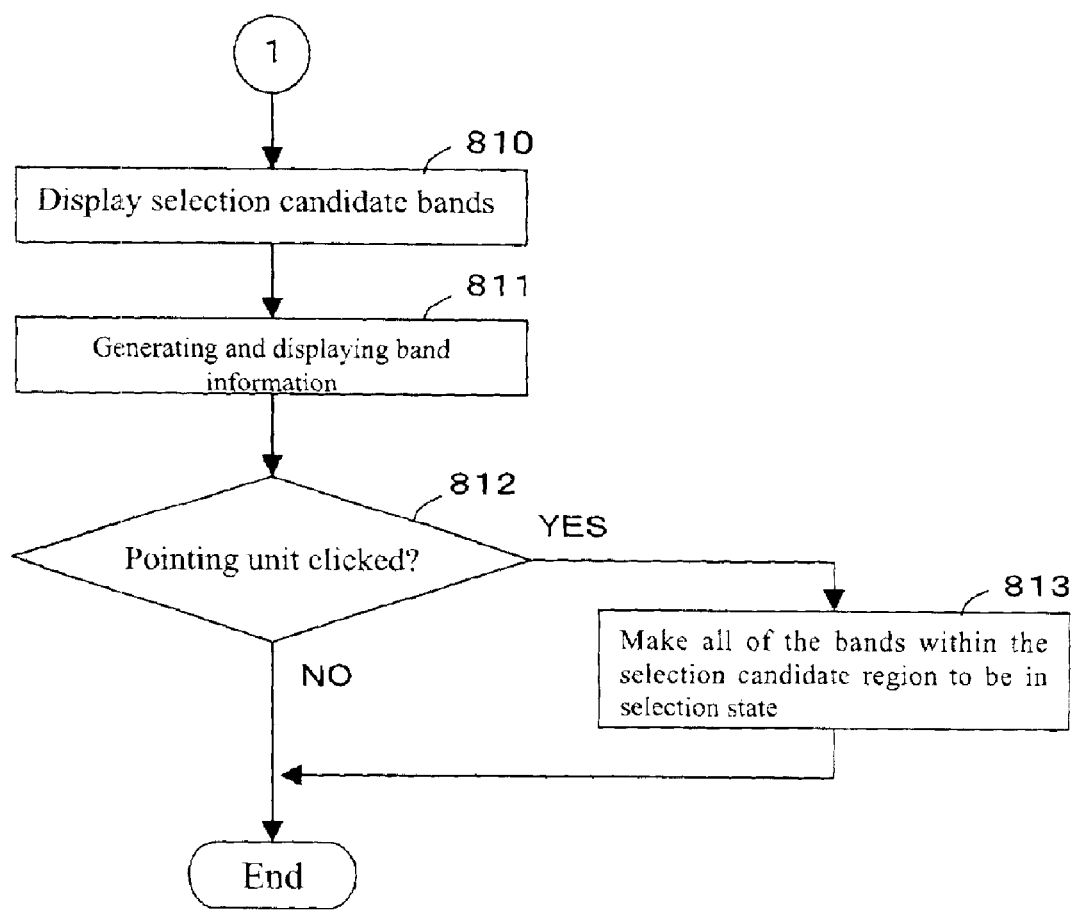
FIG. 9 is a flowchart for showing the general process under the all-band selection mode.

FIGS. 8 and 9 are flowcharts showing the whole process under the all-band selection mode. In Step 801, whether or not the "5" key of the keyboard is pressed is checked. If the "5" key is determined to be pressed, the process proceeds to Step 802 to switch to the single-band selection mode and ends. If the "5" key is determined to be unpressed, the process proceeds to Step 803. In Step 803, whether or not the "0" key of the keyboard is pressed is checked. If the "0" key is determined to be pressed, the process proceeds to Step 804 to switch to the normal mode and ends. If the "0" key is determined to be unpressed, the process proceeds to Step 805.

In Step 805, the center coordinates of the selection candidate region are input with the pointing unit. Specifically, the input cursor of the pointing unit is moved to a desired position on a desired lane. In Step 806, the selection candidate region is displayed where the coordinates input at Step 805 is set at the center. In Step 807, whether an arrow key of the keyboard is pressed is checked. When the arrow key is determined to be pressed, the process proceeds to Step 808 to perform an enlargement/reduction operation 808 for the selection candidate region. The enlargement/reduction operation 808 will be described below with reference to FIG. 12. In the subsequent Step 809, selection candidates determination and settings for the all-band selection mode are performed.

In the following Step 810, the bands set as the selection candidates are displayed. In the next Step 811, information of the bands in the selection candidate region is generated and displayed. In Step 812, whether or not clicking operation is performed with the pointing unit is checked. If a click with the pointing unit is determined to have taken place, the process proceeds to Step 813. In Step 813, the bands within the selection candidate region are displayed in a selection state.

Figure 10:
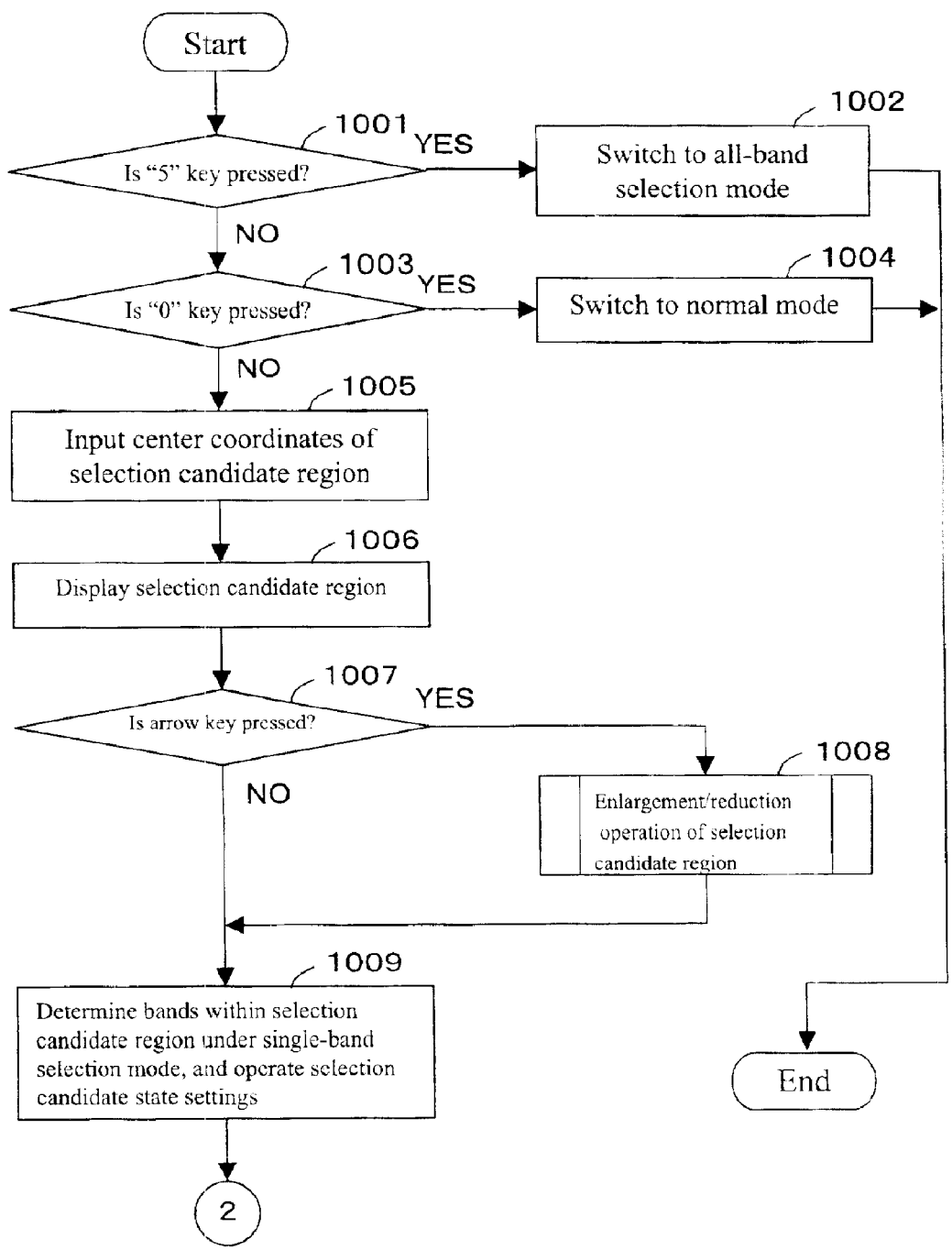
FIG. 10 is a flowchart for showing a general process under the single-band selection mode.
Figure 11:
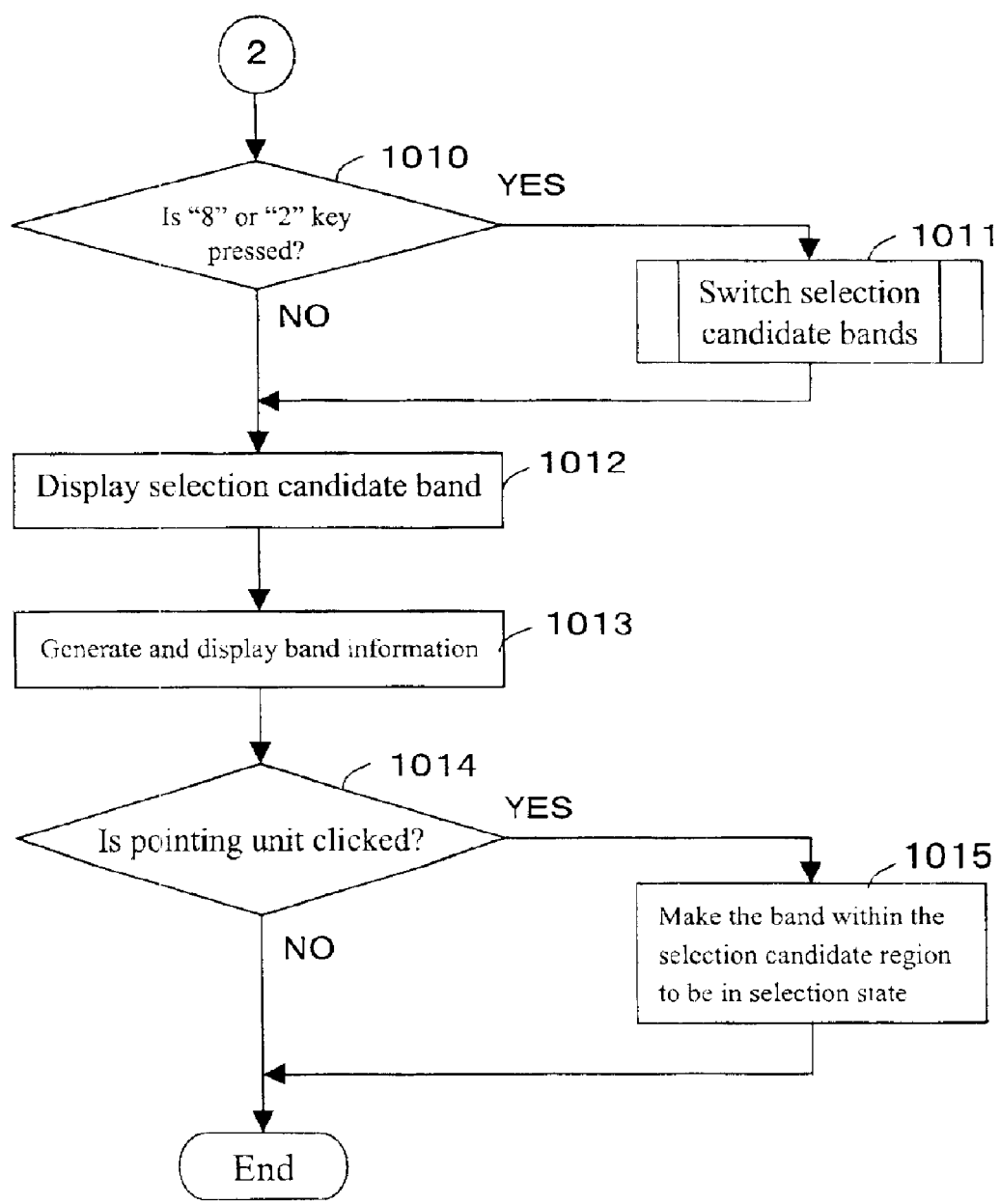
FIG. 11 is a flowchart for showing the general process under the single-band selection mode.

FIGS. 10 and 11 are flowcharts showing the whole process under the single-band selection mode. In Step 1001, whether or not the "5" key of the keyboard is pressed is checked. If the "5" key is determined to be pressed, the process proceeds to Step 1002 to switch to all-band selection mode and ends. If the "5" key is determined to be unpressed, the process proceeds to Step 1003. In Step 1003, whether or not the "0" key of the keyboard is pressed is checked. If the "0" key is determined to be pressed, the process proceeds to Step 1004 to switch to the normal mode and ends. If the "0" key is determined to be unpressed, the process proceeds to Step 1005.

In Step 1005, the center coordinates of the selection candidate region are inputted with the pointing unit. Specifically, the input cursor of the pointing unit is moved to a desired position on a desired lane. In Step 1006, the selection candidate region is displayed where the coordinates input at Step 1005 is set at the center. In Step 1007, whether an arrow key of the keyboard is pressed is checked. When the arrow key is determined to be pressed, the process proceeds to Step 1008 to perform an enlargement/reduction operation 1008 for the selection candidate region. The enlargement/reduction operation 1008 will be described below with reference to FIG. 12. In the subsequent Step 1009, selection candidates determination and settings for the single-band selection mode are performed.

In the following Step 1010, whether or not the "8" or "2" key of the keyboard is pressed is checked. If the "8" or "2" key is determined to be pressed, the process proceeds to Step 1011 and switching operation 1011 takes place for the selection candidate band displayed under the single-band selection mode. Details of the switching operation 1011 for the selection candidate band will be described with reference to FIG. 17. In the following Step 1012, the bands set as the selection candidates are displayed. In the next Step 1013, information of the band in the selection candidate region is generated and displayed. In Step 1014, whether or not a clicking operation by the pointing unit is performed is checked. If the clicking operation by the pointing unit is determined to have taken place, the process proceeds to Step 1015. In Step 1015, the bands within the selection candidate region are displayed in a selection state.

Figure 12:
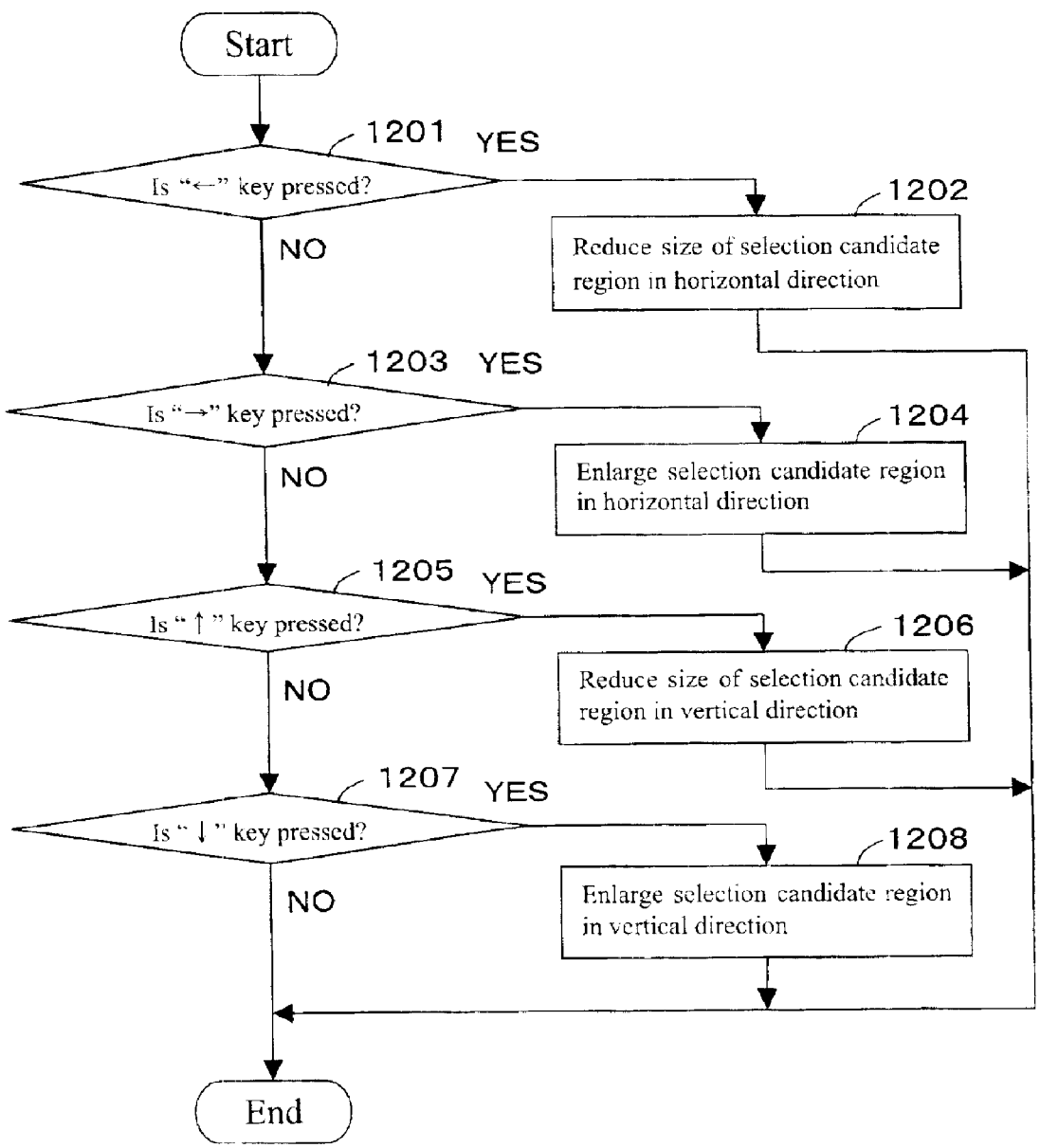
FIG. 12 is a flowchart showing an enlargement/reduction operation of a selection candidate region.

FIG. 12 is a flowchart for showing the enlargement/reduction operation of the selection candidate region by a keyboard input under the all-band selection mode and the single-band selection mode. In Step 1201, whether or not the "(left pointing arrow)" key is pressed is checked. If the "(left pointing arrow)" key is determined to be pressed, the operation proceeds to Step 1202 to reduce the size of the selection candidate region in horizontal direction and ends the operation. As shown in FIGS. 13A and 13B, when this operation is performed for the selection candidate region 1301, the size of the region 1301 is reduced in the horizontal direction while the position of the cursor 1302 is set at the center, thereby setting a new selection candidate region 1311.

If the "(left pointing arrow)" key is determined to be unpressed, the operation proceeds to Step 1203. In Step 1203, whether or not the "(right pointing arrow)" key is pressed is checked. If the "(right pointing arrow)" key is determined to be pressed, the operation proceeds to Step 1204 to enlarge the selection candidate region in horizontal direction and ends the operation. As shown in FIGS. 14A and 14B, when this operation is performed for the selection candidate region 1401, the region 1401 is enlarged in the horizontal direction while the position of the cursor 1402 is set at the center, thereby setting a new selection candidate region 1411.

If the "(right pointing arrow)" key is determined to be unpressed, the operation proceeds to Step 1205. In Step 1205, whether or not the "(up pointing arrow)" key is pressed is checked. If the "(up pointing arrow)" key is determined to be pressed, the operation proceeds to Step 1206 to reduce the size of the selection candidate region in vertical direction and ends the operation. As shown in FIGS. 15A and 15B, when this operation is performed for the selection candidate region 1501, the size of the region 1501 is reduced in the vertical direction while the position of the cursor 1502 is set at the center, thereby setting a new selection candidate region 1511.

If the "(up pointing arrow)" key is determined to be unpressed, the operation proceeds to Step 1207. In Step 1203, whether or not the "(down pointing arrow)" key is pressed is checked. If the "(down pointing arrow)" key is determined to be pressed, the operation proceeds to Step 1208 to enlarge the selection candidate region in vertical direction. As shown in FIGS. 16A and 16B, when this operation is performed for the selection candidate region 1601, the region 1601 is enlarged in the vertical direction while the position of the cursor 1602 is set at the center, thereby setting a new selection candidate region 1611.

Figure 17:
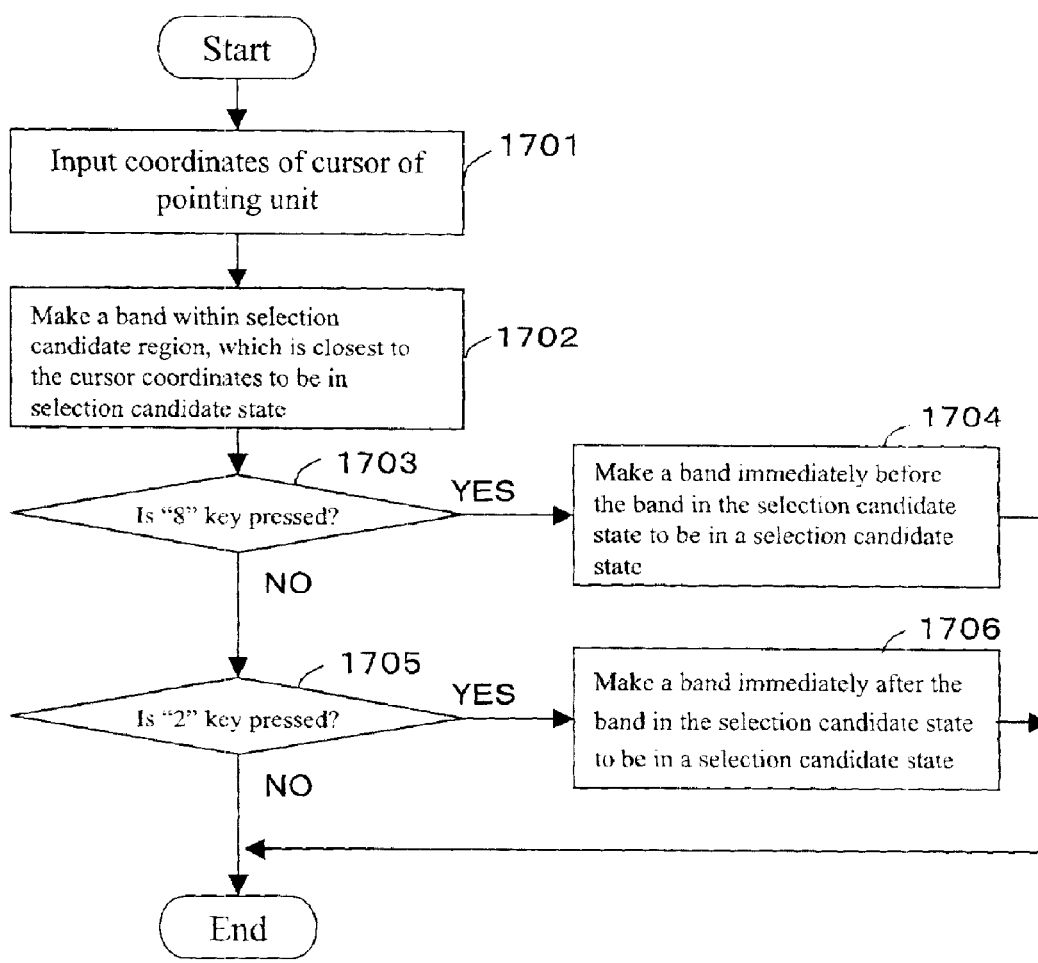
FIG. 17 is a flowchart showing an operation of switching a band to be in a selection candidate state under the single-band selection mode.
Figure 19:
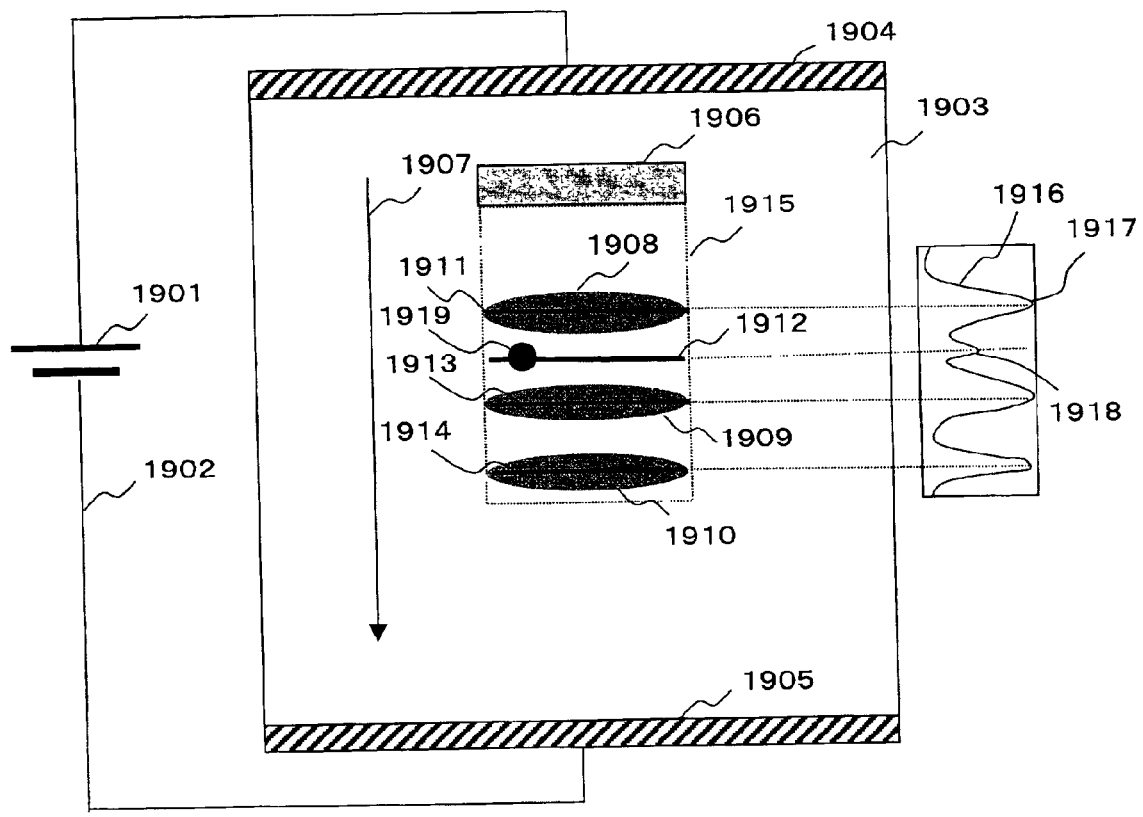
FIG. 19 is a schematic diagram for illustrating electrophoresis bands and lanes, and migration of DNA molecules.

FIG. 17 is a flowchart showing the switching operation of a selection candidate band by a keyboard input under the single-band selection mode. In Step 1701, cursor coordinates are input with the pointing unit. In Step 1702, the band closest to the cursor coordinates input in Step 1701 is processed to be in a selection candidate state. In Step 1703, whether or not the "8" key of the keyboard is pressed is checked. If the "8" key is determined to be pressed, the operation proceeds to Step 1704, where a band immediately before the band in the selection candidate state (with respect to the electrophoresis direction) is set to be in the selection candidate state, and end the operation. If the "8" key is determined to be unpressed in Step 1703, the operation proceeds to Step 1705. In Step 1705, whether the "2" key of the keyboard is pressed is checked. If the "2" key is determined to be pressed, the operation proceeds to Step 1706 where the band immediately after the band in the selection candidate state (with respect to the electrophoresis direction) is set to be in the selection candidate state, and end the operation. If the "2" key is determined to be unpressed in Step 1705, the operation is ended.

By employing the present invention, only the band of interest can be selected from a group of gathering bands so that the selected band may be processed (e.g., deleted). Although specific keys are assigned for particular operations in the above description, these keys are only examples for clearer understanding of the invention. The present invention is not limited to the specific examples described herein.

According to the present invention, by using the keyboard and the pointing unit of the interactive input unit, a band on a screen may be displayed in a selection state in a simple and efficient manner.

What is claimed is:

1. A device for selecting an electrophoresis band of interest from a plurality of bands on an electrophoresis lane of a sample, the device comprising:

a display unit for displaying an image of the plurality of bands established on the lane;

a region setting unit for setting a region on the lane on a screen of the display unit;

a band information displaying unit for displaying the number of bands in a selection candidate state relative to the region;

a region altering unit for altering a display size of the region and for altering band information including the number of bands in the selection candidate state in response to the altered display size of the region;

a selection candidate displaying unit for displaying bands within the region in the selection candidate state; and a band selecting unit for processing the bands in the selection candidate state to be in a selection state.

2. A device for selecting an electrophoresis band according to claim 1, wherein the region setting unit sets the region on the lane by setting an input cursor of a pointing unit on the lane at the center, and the region altering unit alters the display size of the region in accordance with the press of a predetermined key of a keyboard.

3. A device for selecting an electrophoresis band of interest from a plurality of bands on an electrophoresis lane of a sample, the device comprising:

a display unit for displaying an image of the plurality of bands established on the lane;

a region setting unit for setting a region on the lane on a screen of the display unit;

a band information displaying unit for displaying the number of bands in a first selection candidate state relative to the region;

a region altering unit for altering a display size of the region and for altering band information including the number of bands in the first selection candidate state in response to the altered display size of the region;

a selection candidate displaying unit for displaying one of the bands within the region in a second selection candidate state;

a selection candidate display altering unit for altering the band in the second selection candidate state to a band immediately before or after the former band along the lane; and a band selecting unit for processing the band in the second selection candidate state to be in a selection state.

4. A device for selecting an electrophoresis band according to claim 3, wherein the region setting unit sets the region on the lane based on a position of an input cursor of a pointing unit on the lane, the selection candidate displaying unit displays a band closest to the input cursor in the second selection candidate state, and the selection candidate display altering unit alters the band to be displayed in the second selection candidate state in accordance with the press of a predetermined key of a keyboard.

5. A device for selecting an electrophoresis band according to claim 3, wherein the region altering unit alters the display size of the region in accordance with the press of a predetermined key of the keyboard.

6. A method for selecting an electrophoresis band of interest from a plurality of bands on an electrophoresis lane of a sample, the method comprising the steps of:

setting a region on the lane based on an input cursor of a pointing unit placed on the display of the lane having a plurality of bands;

displaying bands within the region in a selection candidate state;

displaying band information including the number of bands in a selection candidate state relative to the region;

altering a display size of the region in accordance with an key input of a predetermined key of a keyboard, as well as altering states of bands that became included in the region as the result of the size alteration from a normal state to the selection candidate state and states of bands that fell out from the region as the result of the size alteration from the selection candidate state to the normal state;

altering the band information including the number of bands in the selection candidate state in response to altering the display size of the region; and displaying selected bands of the bands in the selection candidate state in a selection state in response to a selection input.

7. A method for selecting an electrophoresis band of interest from a plurality of bands on an electrophoresis lane of a sample, the method comprising the steps of:

setting a region on the lane based on an input cursor of a pointing unit placed on the display of the lane having a plurality of bands;

displaying band information including the number of bands in a first selection candidate state relative to the region;

altering a display size of the region and altering band information including the number of bands in the first selection candidate state in response to altering the display size of the region;

displaying a band within the region, which is closest to the input cursor, in a second selection candidate state;

altering the band in the second selection candidate state to a band immediately before or after the former band along the lane in accordance with the press of a predetermined key of a keyboard; and processing the band in the second selection candidate state to be in a selection state.

8. A device for selecting an electrophoresis band according to claim 4, wherein the region altering unit alters the display size of the region in accordance with the press of a predetermined key of the keyboard.

* * * * *